(12) United States Patent
Ono

(10) Patent No.: US 10,513,684 B2
(45) Date of Patent: Dec. 24, 2019

(54) MANUFACTURING METHOD AND DEVICE FOR THREE-DIMENSIONAL ENGINEERED TISSUE

(71) Applicant: Jiro Ono, Saitama (JP)

(72) Inventor: Jiro Ono, Saitama (JP)

(*) Notice: Subject to any disclaimer, the term of this patent is extended or adjusted under 35 U.S.C. 154(b) by 106 days.

(21) Appl. No.: 15/920,082

(22) Filed: Mar. 13, 2018

(65) Prior Publication Data

US 2018/0223252 A1 Aug. 9, 2018

Related U.S. Application Data

(63) Continuation of application No. PCT/JP2016/076987, filed on Sep. 13, 2016.

(51) Int. Cl.
*C12N 5/00* (2006.01)
*A61L 27/38* (2006.01)
*C12M 1/00* (2006.01)
*C12M 3/06* (2006.01)

(52) U.S. Cl.
CPC ........ *C12N 5/0068* (2013.01); *A61L 27/3895* (2013.01); *C12M 1/00* (2013.01); *C12M 27/16* (2013.01); *C12N 5/0062* (2013.01); *C12N 2513/00* (2013.01); *C12N 2535/00* (2013.01)

(58) Field of Classification Search
None
See application file for complete search history.

(56) References Cited

U.S. PATENT DOCUMENTS

| | | | |
|---|---|---|---|
| 8,852,932 B2 | 10/2014 | Forgacs et al. | |
| 2008/0194010 A1 | 8/2008 | Liu | |
| 2011/0233148 A1* | 9/2011 | Antonchuk | B01D 39/1692 210/772 |
| 2013/0306576 A1* | 11/2013 | Bosio | B01D 35/306 210/767 |
| 2014/0283356 A1* | 9/2014 | Nakayama | C12M 25/14 29/428 |

FOREIGN PATENT DOCUMENTS

| | | |
|---|---|---|
| JP | 2004321065 A | 11/2004 |
| JP | 2005532030 A | 10/2005 |
| JP | 4122280 B2 | 7/2008 |
| JP | 2009031300 A | 2/2009 |

(Continued)

OTHER PUBLICATIONS

Do et al., "3D Printing of Scaffolds for Tissue Regeneration Applications", Adv Healthc Mater, 2015, 4(12), pp. 1742-1762. (Year: 2015).*

(Continued)

*Primary Examiner* — Laura Schuberg
(74) *Attorney, Agent, or Firm* — McDonnell Boehnen Hulbert & Berghoff LLP

(57) ABSTRACT

A method for fabricating a cellular structure is disclosed. The method includes feeding cell aggregates onto a plurality of thread or needle shaped members in each of a plurality of supports. Each member forms net or mesh shaped spaces in the respective support. The method also includes layering the supports with the cell aggregates fed therein, culturing the cell aggregates to fuse, and removing the plurality of thread or needle shaped members from the fused cellular structure.

20 Claims, 19 Drawing Sheets

(56) References Cited

FOREIGN PATENT DOCUMENTS

| JP | 2010517590 A | | 5/2010 |
|---|---|---|---|
| JP | 2015057961 A | | 3/2015 |
| JP | 2017063729 A | | 4/2017 |
| JP | 2017079719 A | | 5/2017 |
| WO | 03031065 A1 | | 4/2003 |
| WO | 2005047496 A1 | | 5/2005 |
| WO | 2008123614 A1 | | 10/2008 |
| WO | 2008143149 A1 | | 11/2008 |
| WO | 2013073672 A1 | | 5/2013 |
| WO | WO 2016069892 | * | 5/2016 |
| WO | 2017150366 A1 | | 9/2017 |

OTHER PUBLICATIONS

Jakab, Karoly, et al., "Relating Cell and Tissue Mechanics: Implications and Applications", Developmental Dynamics 237:2438-2449, Jun. 25, 2008.

Itoh, Manabu, et al., "Scaffold-Free Tubular Tissues Created by a Bio-3D Printer Undergo Remodeling and Endothelialization when Implanted in Rat Aortae", PLoS One 10(9): e0136681. doi:10.1371/journal.pone.0136681; Sep. 1, 2015; 15 pages.

Jakab, Karoly, et al., "Engineering biological structures of prescribed shape using self-assembling multicellular systems", PNAS, vol. 101, No. 9; Mar. 2, 2004; pp. 2864-2869.

Pérez-Pomares, José M., et al., "Tissue fusion and cell sorting in embryonic development and disease: biomedical implications", BioEssays 28.8; 2016; pp. 809-821.

Gordon, Richard, et al., "A Rheological Mechanism Sufficient to Explain the Kinetics of Cell Storing", Journal of Theoretical Biology; Nov. 1972; pp. 43-73.

Mironov, Vladimir, et al., "Organ printing: Tissue spheroids as building blocks", Biomaterials; Apr. 2009; 30(12): 2164-2174. doi:10.1016/j.biomaterials.2008.12.084; 22 pages.

* cited by examiner

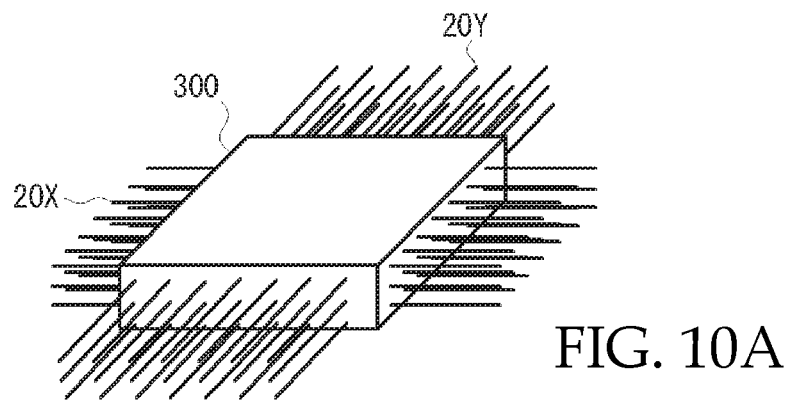
FIG. 10A
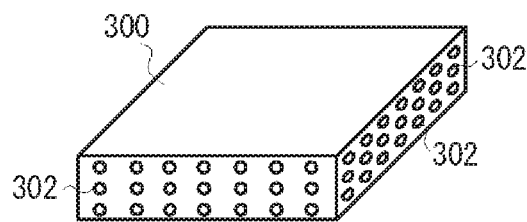
FIG. 10B
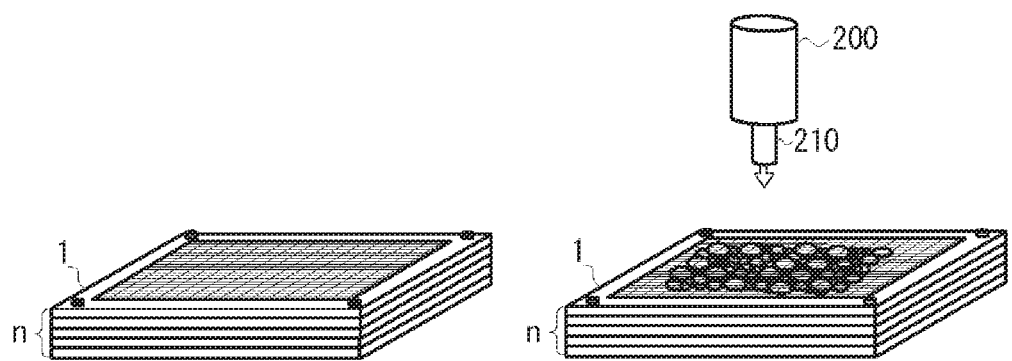
FIG. 11A
FIG. 11B

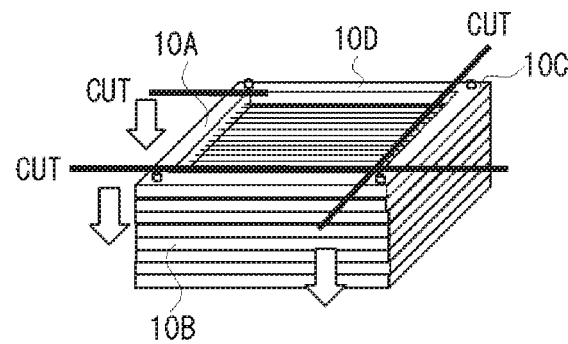
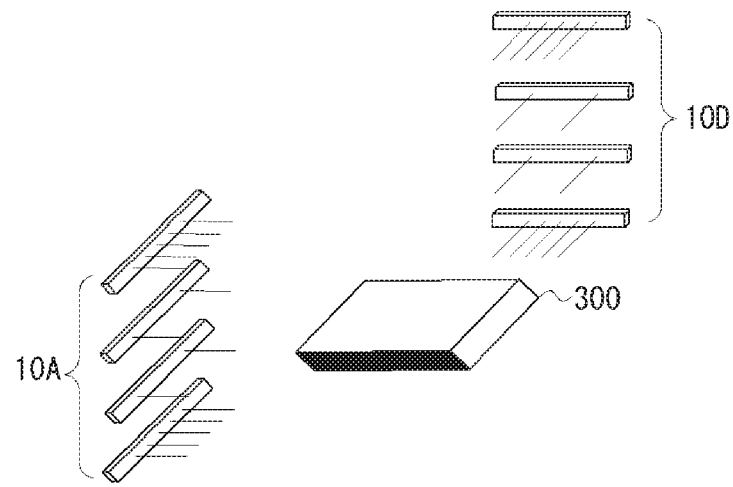
FIG. 13C        FIG. 13D
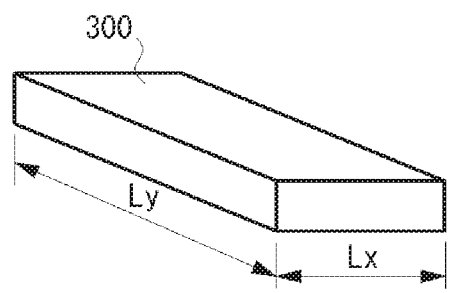
FIG. 14

MANUFACTURING METHOD AND DEVICE FOR THREE-DIMENSIONAL ENGINEERED TISSUE

CROSS-REFERENCE TO RELATED APPLICATIONS

This application is a continuation of co-pending International Application No. PCT/JP2016/076987, which was filed on Sep. 13, 2016 and is incorporated herein by reference.

TECHNICAL FIELD

This invention relates generally to the field of fabricating of three-dimensional engineered tissue using cell aggregates, especially the method of fabricating three-dimensional engineered tissue using the net-like shape or mesh-like supports.

BACKGROUND

As world population increases as well as prolonged human lifetime span, needs, desires and demands for medical treatments are only elevating. In recent years, a new approach, Tissue Engineering, which utilizes living cell, is spotlighted. The ultimate goal of Tissue Engineering is to fabricate artificial tissue and organ for transplantation to human body. Artificial tissue is fabricated part of the body which expresses particular functionality when transplanted to human body. However, transplantation to human body requires number of approving process which comes with long span activities.

Aside from human transplantation, another promising application is to use engineered tissue as research specimen, which includes toxicity screening, drug effect judgement, pathology judgement, developmental research, etc. By fabricating engineered tissue with only human cells and using them for experimentation, it will be possible to reproduce or mimic in vivo environment of human body. This leads to higher drug discovery research, personalized medication diagnosis and development observations, etc.

Especially in the field of cancer, medication diagnosis and effect prediction is always difficult one. This technology may enable better prediction when text specimen is made with patient own cancer cells and tested number of different drugs ex-vivo, or outside of the body, prior to actual medications.

There are two types of cells, one is floating cell and another is adherent cell which required scaffold. Floating cell includes blood cells and immune system, and adherent cell are organ, skin and bone cells. Adherent cell shall not be able to survive in long period when floating in cell suspension, and it is necessary to let them adhere to any scaffold such as dish or gel and such so that they can survive and proliferate. When adherent cell is located in non-adherent environment, which means there are nothing to adhere to, cells seek for scaffold and start adhering each other and consequently forms large cell aggregate, which is three-dimensional cellular structure. This phenomenon is widely known and reported in non-patent articles 1~6. Non-patent article 1 describes this cell aggregating phenomenon is known as old as 1960's. Especially non-patent article 6 clarifies the idea using cell aggregate as "Building Block" which indicates that diversified type of cell could be used.

Japanese patent document JP-P4122280 describes a method of fabricating tissue plug from only living cell with desired shape without support. In detail, this process uses a chamber which possess micro-pore only at the bottom which enable medium to pass through, and apply just enough mediums inside of chamber so that part of cell aggregate are exposed to air, use in excess of medium of total chamber volume for maturation of cellular structure.

Also, there are number of methods of making three-dimensional cellular structure. U.S. Pat. No. 8,852,932 describes dispensing method which dispenses cell aggregate onto plane surface from printer nozzle, whereas PCT publication WO2017/150366 A1 (PCT/JP2017/00729) shows a process needle array process which penetrates through Spheroids as needed. The needle array process use support consists of a number of needles mounted on base, which needles penetrate number of spheroids for alignment, and remove needles after the maturation to obtain 3D cellular structure. Furthermore, PCT publication WO2005/047496 shows process of making 3D Cellular structure by accumulating multiple plane cultured cell sheets which was made on permeable sheet.

The following non-patent literature is also related to subject matter disclosed herein:

PLOS ONE, Journal. Pone. 0136681, "Scaffold-Free Tubular Tissues Created by a Bio-3D printer Undergo Remolding and Endothelialization when Implanted in Rat Aortae," Manabu Itoh et al, Sep. 1, 2015;

Gordon R, Goel N S, Steinberg M S, Wiseman L L. A rheological mechanism sufficient to explain the kinetics of cell sorting. J Theor Biol. 1972; 37:43-73. [PubMed: 4652421];

Jakab K, Damon B, Marga F, Doaga O, Mironov V, Kosztin I, Markwald R, Forgacs G. Relating cell and tissue mechanics: implications and applications. Dev. Dyn. 2008; 237:2438-2449. [PubMed: 1872 9216];

Jakab K, Neagu A, Mironov V, Markwald R R, Forgacs G. Engineering biological structures of prescribed shape using self-assembling multicellular systems. Proc Natl Acad Sci USA. 2004; 101:2864-2869. [PubMed: 14981244];

Perez-Pomares J M, Foty R A. Tissue fusion and cell sorting in embryonic development and disease: biomedical implications. Bioessays. 2006; 28:809-821. [PubMed: 16927301]; and Organ printing: Tissue spheroids as building blocks" Biomaterials. Vladimir Mironov, Richard P. Visconti, Vladimir Kasynocv, Gabor Forgacs, Christopher J. Drake, and Roger R. Markwald, 2009 April; 30(12):2164-2174. doi: 10.101016.

SUMMARY

Embodiments of the invention relate generally to the field of fabricating of three-dimensional engineered tissue using cell aggregates, for example, a method of fabricating three-dimensional engineered tissue using net-like shape or mesh-like supports.

Most dispensing methods for three-dimensional cellular structure fabrication such as described in U.S. Pat. No. 8,852,932 are either a process which dispense Bio-Ink, which consists of spheroid and connecting material such as Hydrogel or collagen, onto flat surface, or a process injecting spheroids into pre-build scaffold made with shape maintaining material which can be Hydrogel or Collagen. The downside of this method is that scaffold material block oxygen and nutrients delivery to cells. Furthermore, this patent document claims to "arrange a plurality of cell aggregates according to a pattern such that each of the cell aggregates contacts at least one other cell aggregate," which requires "arranging according to a pattern." Also, as shape of these types of three-dimensional cellular structure depends largely on shape retaining capability of scaffold materials, there are limitation in size and shape (especially height direction). Furthermore, Scaffold will remain inside of three-dimensional Cellular structure, that leaves possibility of potential adverse effect against cell, which causes additional evaluation or approval process when transplanted to human patient.

PCT publication WO/2017150366 describes a needle array process which has predetermined separation distance of each needle, several conditions toward cell aggregate are required, such as, cell aggregate has to be sphere shape in general, soft enough that needle can pierce through as well as hard enough that cell aggregate remain at the same position on the needle, and cell aggregate size has to be within certain range so that they shall be contacting each other on the needle. As this process picks a place cell aggregate one at a time, total operation time shall be considerably long. Furthermore, precise needle location is essential to this process and that requires precise manufacturing, which lead to higher manufacturing cost as well as special equipment to handle needle array.

Embodiments of the present invention can solve the above mentioned problems and provide a better and easier method of fabricating three-dimensional cellular structure and supporting device ding the same.

Embodiments provide a method of fabricating three-dimensional cellular structure. The method comprises a step of feeding cell aggregate onto thread or needle shaped members. The member forms meshed space by the thread or needle shaped members. The method also comprises a step of layering the supports with fed cell aggregate, and a step of removing the threads or needles from fused cellular structure.

Embodiments also provide a method of fabricating cellular structure. The method comprises a step of layering supports having meshed space formed by thread or needle shaped members, a step of feeding cell aggregate onto the layered support, and a step of removing the thread or needle shape members from fused cellular structure.

Embodiments also provide a support used for three-dimensional cellular structure in present invention comprises multiple frames, multiple thread or needle shaped members which form net shaped space surrounded by multiple frames, and the net shaped space can hold cell aggregates.

Embodiments also provide a method of fabricating cellular structure utilizing automated dispensing equipment. The method comprises a step of preparing support comprise multiple thread or needle shaped members which form net shaped space, a step of holding cell aggregates being fed from the automated dispensing equipment within the net shaped space after, and a step of removing thread or needle shaped member from fused cell aggregate.

Embodiments also provide a method of making support described in present invention comprises forming a mask layer onto thin sheet member, and forming thread or needle shaped member by etching exposed area of the thin sheet member. Furthermore, a method of making support described in present invention comprises forming thread or needle shaped members by bonding wire.

Embodiments of the present invention provide an easier fabrication method compared to existing methods, by enabling to remove thread or needle shaped member one by one from cell aggregate after the cell aggregates fused together, wherein the aggregate filled into the space which is formed by thread or needle shaped members.

BRIEF DESCRIPTION OF THE DRAWINGS

FIG. 10A shows schematic perspective view of three-dimensional cellular structure after frame of support.

FIG. 10B shows schematic perspective view of three-dimensional cellular structure after thread shaped member are removed.

FIGS. 11A and 11B provide a one modification example of present invention, which shows dispensing after multiple supports are being layered.

FIGS. 13C and 13D provide an example of how thread members are being removed after cutting supports.

FIG. 14 provides a schematic perspective view of three-dimensional cellular structure fabricated using support concerning second embodiment of present invention.

DETAILED DESCRIPTION OF ILLUSTRATIVE EMBODIMENTS

A method of fabricating three-dimensional cellular structure as embodiment of present invention comprises providing a frame and a support with string members (thread or needle shaped) which form net shaped or matrix shaped space inside of the frame, filling the net shaped space with cell aggregate (Spheroid), and removing the string member from fused cellular aggregates to fabricate three-dimensional cellular structure.

Figure 1:
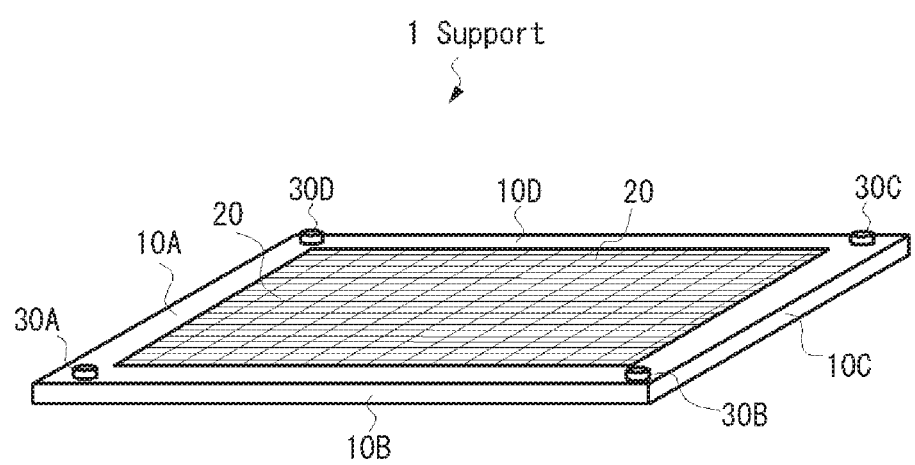
FIG. 1 provides a perspective view of first embodiment of support for three-dimensional cellular structure fabrication.
Figure 2:
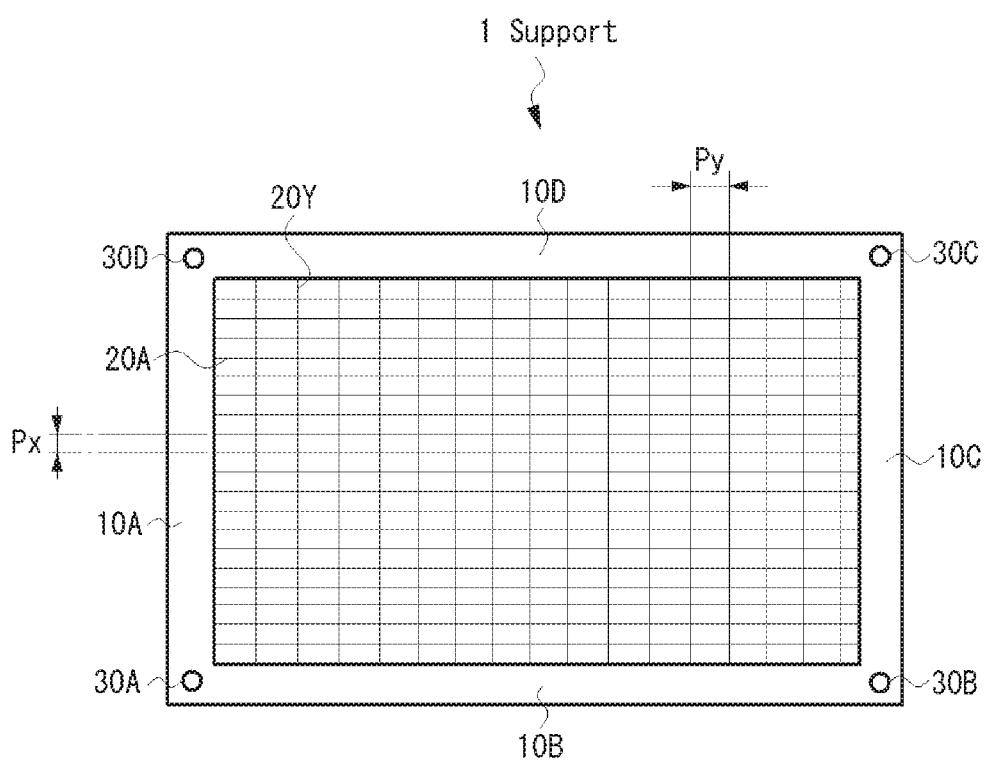
FIG. 2 provides a plan view of the support shown in FIG. 1.
Figure 3:
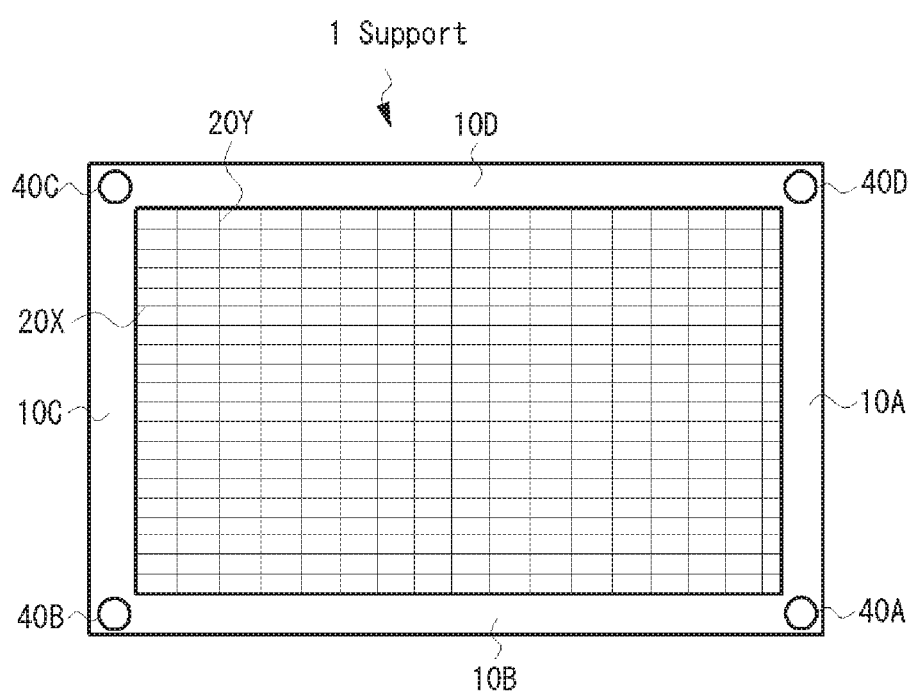
FIG. 3 provides a rear view of the support shown in FIG. 1.

Below are explanations of embodiments. FIG. 1 is perspective view of first embodiment of support for three-dimensional cellular structure fabrication. FIG. 2 is plain view of the support shown in FIG. 1. FIG. 3 is Rear view of the support shown in FIG. 1. Support 1 comprises a frame 10A, frame 10B, frame 10C, and frame 10D forming four side of frame (called hereinafter frame 10 as a whole frame), multiple string member forming net or matrix shaped space inside of frame 10, alignment measure to align each frame when layered.

Frame 10 can be made of arbitrary materials, such as resin. Also, size of frame 10 can be any size, as an example one side length can be 3-4 cm and thickness can be 0.1-1.0 mm when cell aggregate size is around 200 um.

String Member 20 exists in direction of X and Y inside of frame 10. String member 20 can be made with materials such as stainless steel, nylon, polyester, and diameter can be 10 um as one example. Preferably string member 20 is coated with non-adhesive material such as P-HEMA, and sterilized with ethanol. String member 20X existing in x direction connect to frame 10A (by adhesive or such, for example) while another end connected to frame 10C. String member 20Y existing in Y direction connect to frame 10A (by adhesive or such, for example) while another end connected to frame 10C. Multiple String member 20X in x direction are placed at uniform gap distance Px, and multiple String member 20Y in y direction are placed at uniform gap distance Py, consequently both members forming rectangular shaped spaces of Px and Py inside of frame 10. Gap distance Px and Py can be 0.1 mm as an example. Also, ratio of Px and Py can be determined by aspect ratio of frame 10 (for example, Px:Py=4. When aspect ratio of frame 10 is 4:3) but not limited to this ratio.

As explained later, cell aggregates are dispensed onto string member 20 of support 1, and dispensed cell aggregate has to be held at net shaped space formed by string member 20. Thus, the size of net shaped space formed by string member 20 (Px, Py) has to be smaller than the size of cell aggregates to be dispensed. However, uniformity of cell aggregate size is not necessary. It should be noted that simply smallest size of cell aggregate Dmin needed to be larger than Px, Py. (Dmin>Px, Dmin>Py).

Figure 4A:
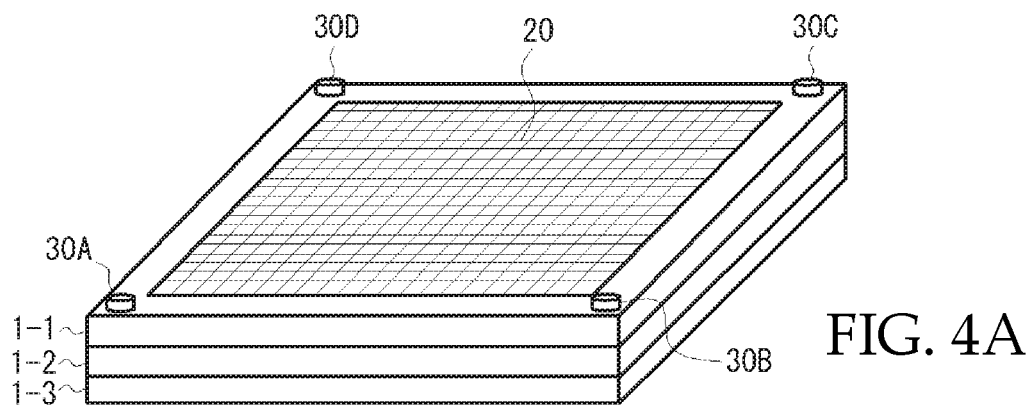
FIGS. 4A-4C provide a perspective view of first embodiment of supports being layered.
Figure 4B:
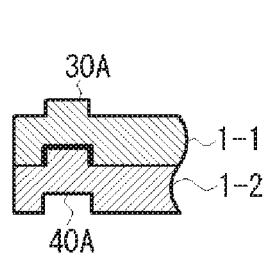
Figure 4C:
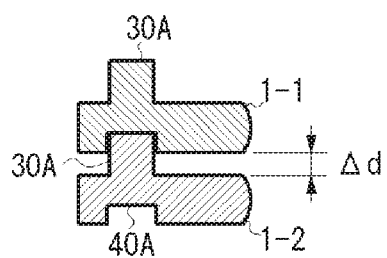

As one of good examples, in order to fabricate three-dimensional cellular structure, identical shaped number of support 1 are layered as shown in FIG. 4A. Support 1 has alignment measure 30 to align each support when layered. Alignment measure 30 can be, but not limited to, dovetail fitting member, fastening by bolts, and other engaging measures. Figure shows cylindrical projections 30A, projection 30B, projection 30C and projection 30D are formed on each corner of support 1, and recess 40A, recess 40B, recess 40C and recess 40D are formed on back side of support 1 which shall engaged to projections 30A, projection 30B, projection 30C and projection respectively. Utilizing these projection 30 and recess 40, layering multiple supports can be easily done. FIGS. 4A-4C show an example of three supports, support 1-1, support 1-2 and support 1-3 are being layered. By selecting height of projection 30 and/or depth of recess 40, arbitrary space between supports can be obtained. FIG. 4B shows projection 30 height is smaller than the depth of recess 40, which consequently forming space Δd between support 1-1 and support 1-2. Ad can be selected depending on thickness of support 1 and/or size of cell aggregate to be dispensed.

Figure 5A:
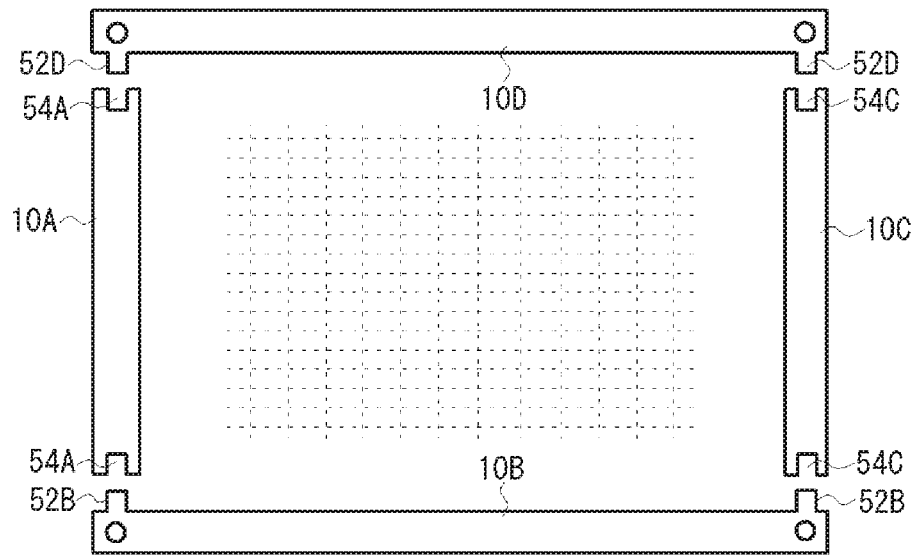
FIGS. 5A and 5B provide an example of how first embodiment of support can be disassembled.

Preferably one of the frames out of multiple frames is detachable from other frames. As explained later, this makes removal of string member 20 from fused sell aggregate easier after cell aggregate fused together. FIG. 5A shows one example how frame is separated from the others. Frame 10A has a recess 54A on both ends; frame 10C has a recess 52B on both ends. Also, frame 10B has a projection 52B on both ends and frame 10D has a projection 52D on both ends. Projection 52B and 52D, recess 54A and 54C engage each other respectively but also detachable. When cell aggregate is dispensed, projection 52B and 52D engage to recess 54A and 54C respectively and four connected frame 10 will form rectangular shape support 1. Later when string member is removed from three-dimensional cellular structure, projection 52B and 52D, recess 54A and 54C are detached, consequently makes four frames separable. Also, when four frames 10 are separated, connection between string member 20 and frame 10 can be released. For example, string member 20 pulled out of frame 10 fixture, and/or cut by knives.

Figure 5B:
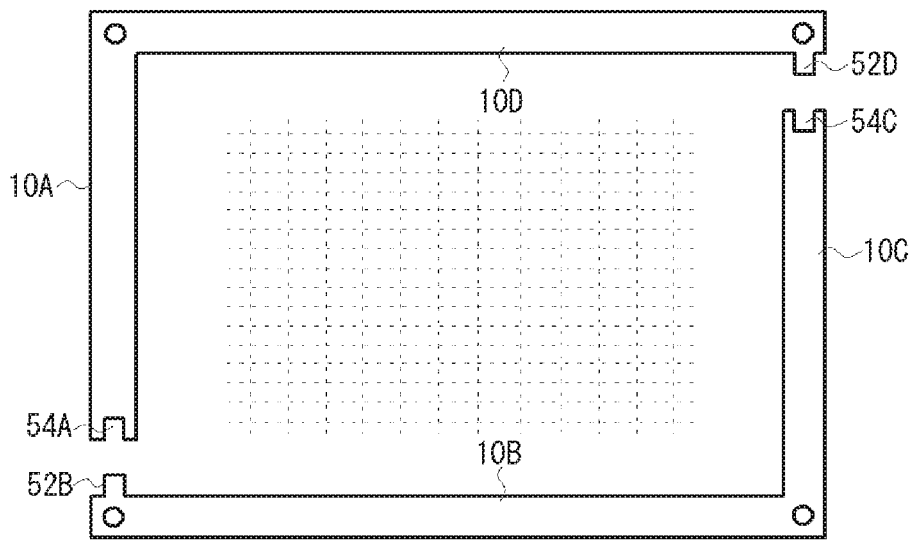

FIG. 5B shows other measure to separate frames. This measure is to separate four frames into two parts. Frame 10A and 10D remain engaged and frame 10B and 10C remain engaged. With this separating method, removal of string member 20 from three-dimensional cellular structure existing in x direction and Y direction is still possible.

Nevertheless, the separating method of the frames is not limited to as described in FIGS. 5A and 5B. For example, when frame 10 is made with soft and easily cuttable materials, frames can be cut by knives, laser and such at multiple cutting locations to separate one frame from another frame, and also, cutting location can be between frame and string member. In this case, frame 10 cannot be reused.

Figure 6:
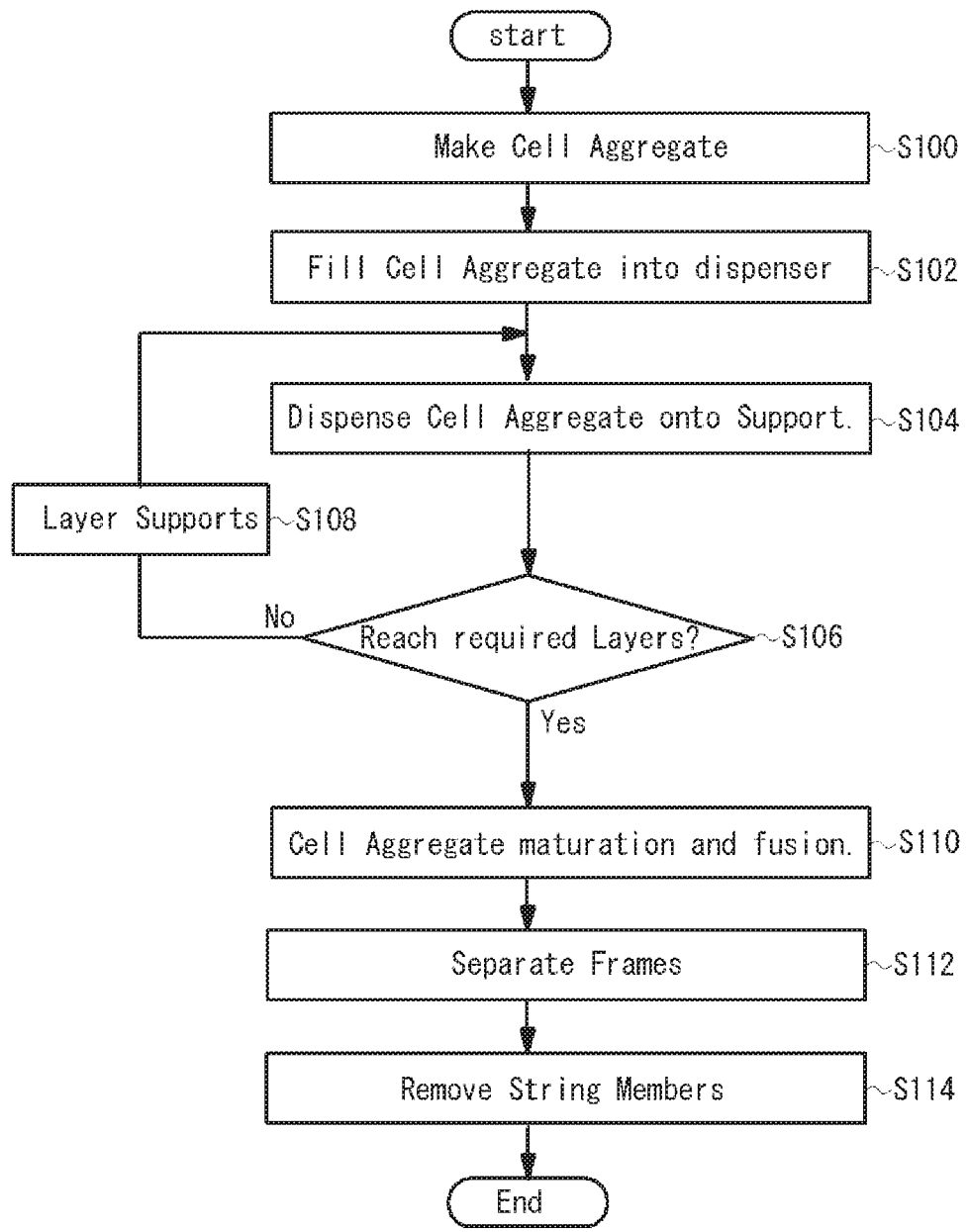
FIG. 6 provides a schematic flow of fabrication process of three-dimensional cellular structure concerning the first embodiment of present invention.

Next, method of three-dimensional cellular structure using support 1 is described using FIG. 6. First, make cell aggregate (Spheroid) in range of certain size by aggregating plurality of living cell (S100). Method of making cell aggregate can be any measure, and one example is described in Patent Document 3.

Figure 7A:
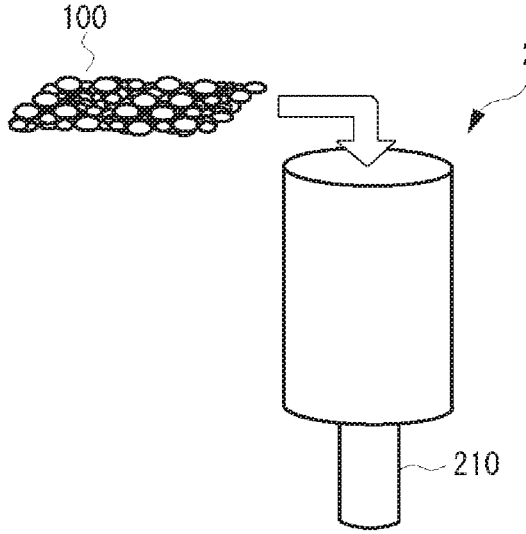
FIGS. 7A and 7B show how cell aggregate are being fed to support.
Figure 7B:
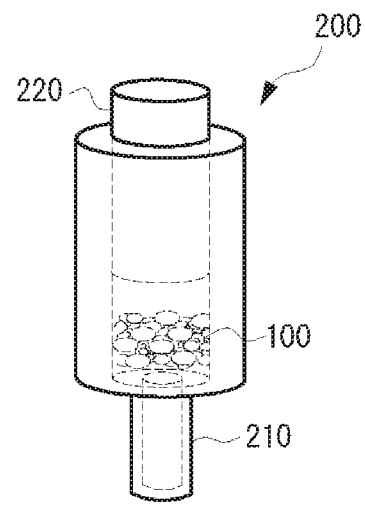

After making cell aggregate, cell aggregate is filled into dispenser (S102). FIG. 7A shows one example how cell aggregate is filled into dispenser. Cell aggregate solution 100 which contains plurality of cell aggregate is filled into dispenser 200. Cell aggregate size contained in cell aggregate solution 100 can be various, but minimum size of cell aggregate Dmin is larger than the space Px and Py width which formed by string member 20. As shown in FIG. 7B, dispenser 200 comprise discharge part 210 and by manipulating cylinder 220 cell aggregate solution 100 can be discharged through discharge part 210.

Figure 8:
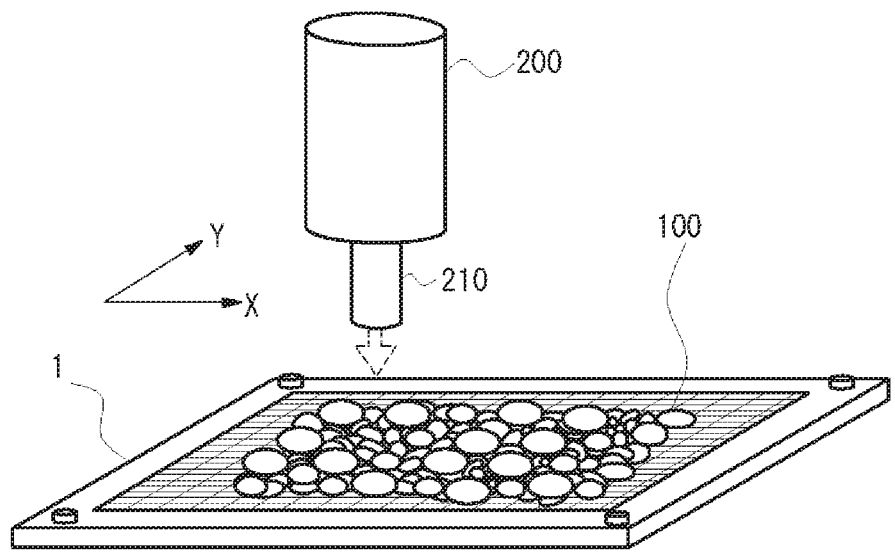
FIG. 8 explains how cell aggregate are being dispensed by dispenser.

Next, Cell aggregate is dispensed onto support surface (S104). As shown in FIG. 8, by scanning to X and Y directions according to desired shape of three-dimensional cellular structure, cell aggregate 100 is dispensed onto string member 20. Other way is to fix location of dispenser 200, and mount support 1 on stage, and move stage 1 to x direction and y direction. The smallest size of cell aggregate Dmin dispensed onto support is larger than Px and Py width and yet dispensed cell aggregate does not go through string member 20 and held by string member 20. It should be noted that part of sphere shape or orbital shape cell aggregate can be protrude through the space of Px, Py toward the bottom.

Figure 9A:
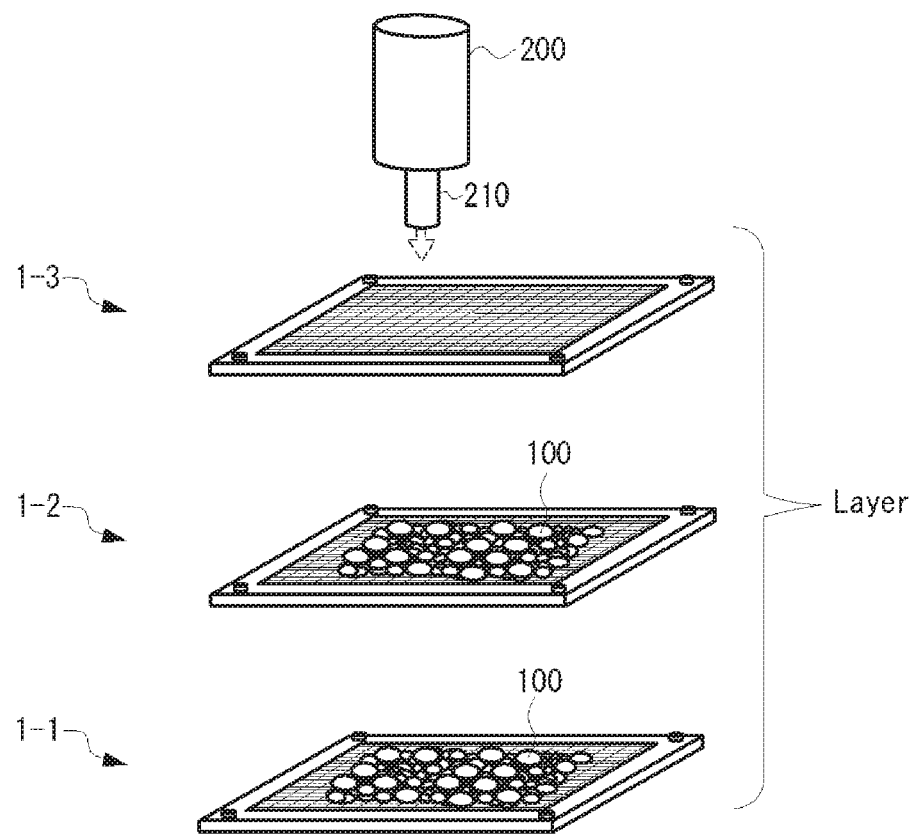
FIGS. 9A and 9B show layering of supports which cell aggregate are already dispensed.
Figure 9B:
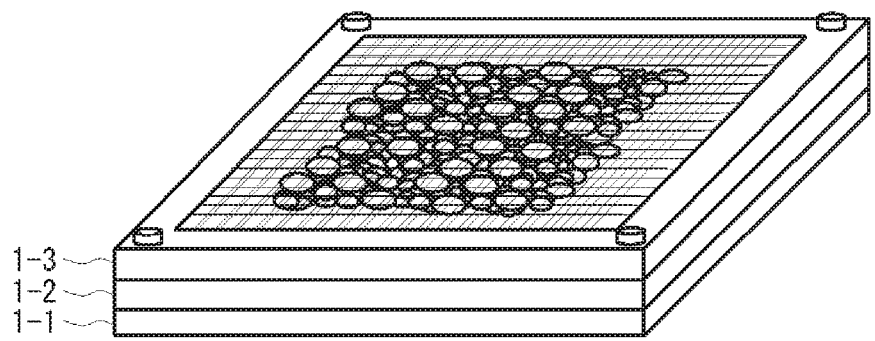

Next, number of layer is monitored (S106). Number of layer is determined by Z axis height of three-dimensional cellular structure to be fabricated. Until given number of layer is completed, additional support is layered (S108) and cell aggregate solution is dispensed onto (S104). When support is layered, each support is aligned by alignment measure 30 and 40, FIG. 9A shows how cell aggregate solution 100 is dispensed onto support 1-1 and 1-2, after completion of dispensing cell aggregate solution 100 onto support 1-2, support 1-3 is layered on top of support 1-2 and cell aggregate solution 100 is dispensed. Thus, multiple supports are layered and cell aggregate solution 100 is dispensed depending on the size of three-dimensional cellular structure to be fabricated. FIG. 9B shows how three support 1-1, 1-2 and 1-3 are layered. When multiple supports are layered, a part of cell aggregate dispensed on upper support can protrude from net space gap downward and have contact to part of cell aggregate dispensed onto lower support.

When a designated number of supports are layered, dispensing cell aggregate solution finishes and they are dipped into medium suitable for cell culture so that cell aggregate fuse together (S110). For example, layered support 1 with cell aggregate is dipped in container filled with medium. At that time, certain vibration or shake can be applied to support and/or container. Cell aggregate on support adhere and fuse together with cell aggregate contacting in horizontal direction. Also, cell aggregates adhere and fuse together with cell aggregate on each layered support in vertical direction. As there is no obstacle to block nutrients and oxygen delivery between cell aggregates dispensed on one support, sufficient nutrients and oxygen reach to cell aggregates. Also, as only string member 20 lie in between cell aggregates on layered support, cell aggregate has access to nutrients and oxygen through the net shaped space. This condition brings ideal environment for cell adhesion and fusion. Time duration shall be determined depending on cell types.

After adhesion and fusion of cell aggregate is completed, frame of layered supports is separated (S112). When separating frames, as of FIGS. 5A and 5B, part or whole frame can be separated, or one end of string member 20 is separated or cut by knives or laser. FIG. 10A shows schematic diagram of fused cell aggregate, which is three-dimensional cell aggregate 300 after all frames are separated. On this schematic diagram, three-dimensional cell aggregate 300 is rectangular parallelepiped shape and possess in its inside multiple string member 20X which lies in X direction and string member 20Y which lies in Y direction, and these string member 20X and string member 20Y stick out from side of three-dimensional cellular structure.

Next step is removal of string member from three-dimensional cellular structure (S114). Preferably, from three-dimensional cellular structure shown in FIG. 10A, string member 20X is removed in X direction, and string member 20Y is removed in Y direction, whole string member is completely removed from three-dimensional cellular structure. FIG. 10B is schematic diagram of three-dimensional cellular structure after removal of string member 20. On each side of three-dimensional cellular structure, there are small pore 302 as the result of removal of string member 20. These small pores 302 will be closed as cell aggregate adhere and fuse together in some time.

As described with respect to the above embodiment, using support which net shaped space is formed inside, dispensing cell aggregate into net shaped space, layer these supports with dispensed cell aggregate, and then removing string member from adhered and/or fused cell aggregate, it is made easier to form plan three-dimensional cellular structure in X and Y direction on one support, and also it is made easier to form thicker three-dimensional cellular structure by layering support in Z direction. Also, cell aggregates are held by very thin diameter string member 20, which blockage of nutrients and oxygen is minimal. Furthermore, string members will be removed from three-dimensional cellular structure, obtained three-dimensional cellular structure does not contain any foreign substance and consequently consists of only required cells.

The above embodiment explained one procedure which cell aggregate is dispensed onto one support and then layered multiple supports, but other procedure is possible such as layering only supports with no cell aggregate is dispensed first, and then dispense cell aggregate onto layered supports. FIG. 11A shows how support 1 are layered by n number, and FIG. 11B shows cell aggregate is dispensed onto from top of support 1 by dispenser 200. Preferably, when this procedure is done, gap distance of support string member Px and Py shall be decreased from top to the bottom. When gap distance of top support string member is Px_max, Py_max, and gap distance of bottom support string member is Px_min, Py_min, size of cell aggregate held by dispenser 200 can be any size between Px_min, Py_min~Px_max, Py_max. From these configurations, cell aggregate which pass through top layer string member space shall be caught by lower string member.

Next a second embodiment of present invention is explained. In the first embodiment, net shaped space is formed on whole support area. In the second embodiment, net shaped space is formed according to arbitrary shape and size of three-dimensional cellular structure.

Figure 12A:
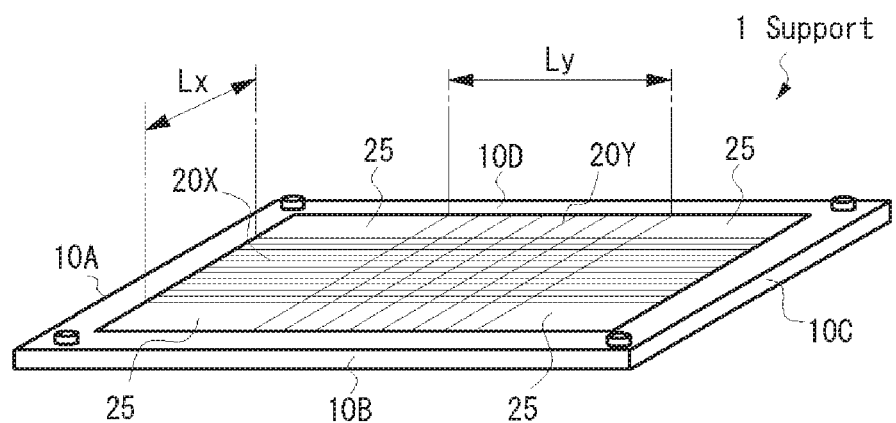
FIG. 12A provides a perspective view showing composition of support concerning the second embodiment of present invention.

FIG. 12A shows schematic diagram of support used for second embodiment. In this embodiment, support 1 has string member 20x in x direction is located in width Lx, and string member 20y in y direction is located in width Ly. From this, support 1 has net shaped space only in between width Lx and Ly. Area 25, which does not have string member, will not hold cell aggregate which is dispensed from dispenser 200. Consequently, three-dimensional cellular structure is formed on Width Lx, Ly area.

Figure 12B:
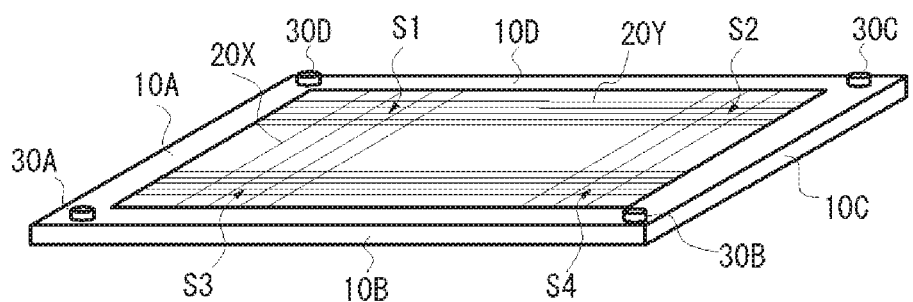
FIG. 12B provides a one modification example of second embodiment of present invention.

The above mentioned example used rectangular space Lx, Ly, but space shape can be different. For example, as shown in FIG. 12B, multiple rectangular space S1, S2, S3 and S4 can be formed inside of support. In this case, four three-dimensional cellular structures which have corresponding shape to S1, S2, S3 and S4 are obtained at one process.

Figure 13A:
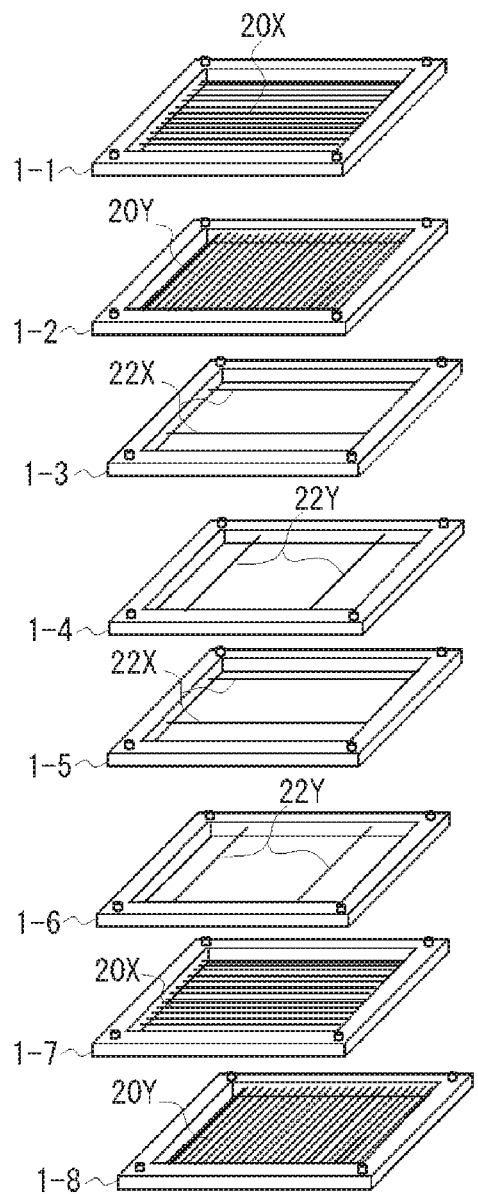
FIGS. 13A and 13B show how cell aggregate are fed onto supports concerning second embodiment of present invention.
Figure 13B:
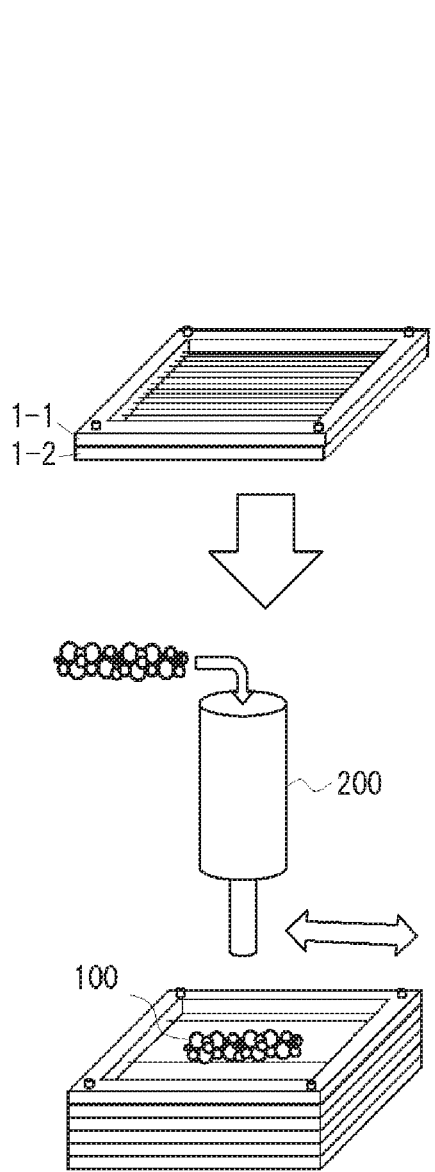

In second embodiment as well as used in first embodiment, multiple support shall be layered according to the height of designed three-dimensional cellular structure. FIGS. 13A and 13B show how supports are layered and cell aggregate are dispensed in second embodiment.

FIG. 13A shows that supports 1-1 and 1-2 make an upper lid and supports 1-7, 1-8 make a bottom lid. The number of Support 1-3~1-6 shall be determined by the height of designed three-dimensional cellular structure. Support 1-1, 1-7 comprise multiple number of string member 20X located in uniform gap distance in X direction, and Support 1-2,1-8 comprise multiple number of string member 20Y located in uniform gap distance in Y direction. Support 1-3 comprise a pair of string member 22X in x direction which regulate the x direction boundary of three-dimensional cellular structure, and Support 1-4 comprise a pair of string member 22Y in y direction which regulate the y direction boundary of three-dimensional cellular structure. Preferably, support 1-3 and 1-4 are layered by each other. Next, as shown on FIG. 13B, cell aggregate is dispensed onto support with Upper Lid 1-1, 1-2 detached. After dispensing is completed, upper Lid 1-1 1-2 is mounted onto Support 1-3.

FIGS. 13C and 13D show one example of how string member is removed. As shown on FIG. 13C, the support is cut at three CUT locations from top to bottom, and separate frame 10B and 10C from the body. And then, as shown on FIG. 13D, move remaining frame 10A to X direction, and move remaining frame 10D to Y direction so that all string member 20 is removed from three-dimensional cellular structure 300.

FIG. 14 is schematic perspective view of three-dimensional cellular structure fabricated by support described in second embodiment. Three-dimensional cellular structure 300 is fabricated at the size of space Lx and Ly which is regulated by string member in X direction and string member in Y direction.

Figure 15A:
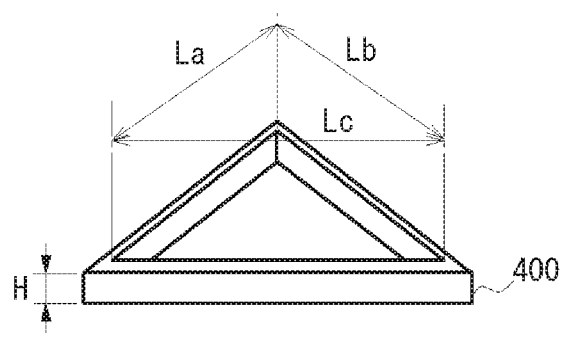
FIGS. 15A and 15B show composition of support concerning third embodiment of present invention.
Figure 15B:
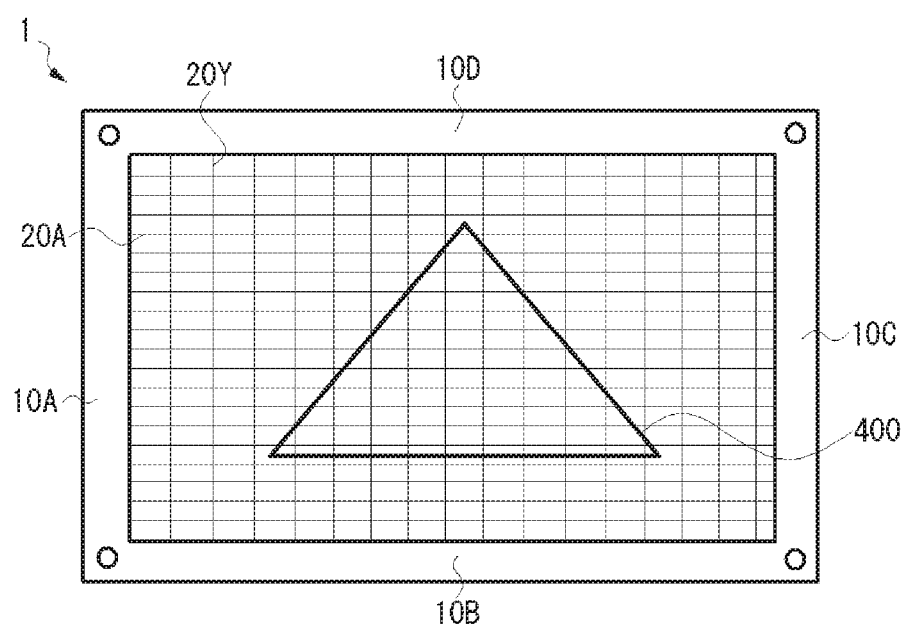

Next, the third embodiment is described. At the third embodiment, guiding member which regulate the shape of cell aggregates to be dispensed into, is provided on a support. FIG. 15A is an example of guiding member 400, and guiding member 400 provides triangle shape of length La, Lb and Lc. The height H of guiding member 400 also functions as spacer Δd between support 1 when layered. Guiding member 400 is mounted onto support at fixed location as shown in FIG. 15B. Fixing measure can be various ways, as one example is to draw marking on support 1 and guiding member 400 is aligned onto support marking. Guiding member 400 can be connected lightly by other fixture or adhesives, or simply placed on the support. Also, preferably guiding member surface s coated with non-adherent material for easy removal from cell aggregate.

Figure 16:
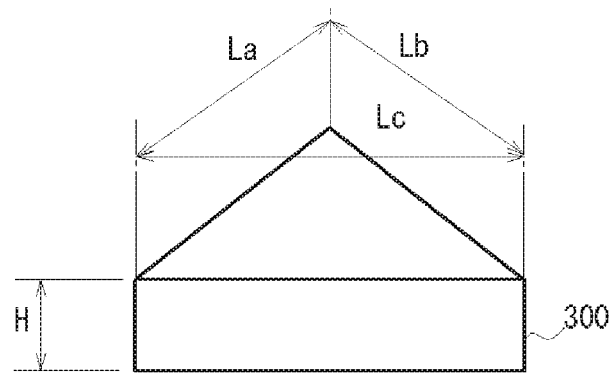
FIG. 16 provides a schematic perspective view of three-dimensional cellular structure fabricated using support concerning third embodiment of present invention.

As shown in FIG. 15B, dispense 200 dispense cell aggregate into the space guided by guiding member 400. Next, other support is layered and guiding support 400 is also placed, and cell aggregate is dispensed into as well. Consequently as shown in FIG. 16, Three-dimensional cellular structure 300 is obtained.

Figure 17A:
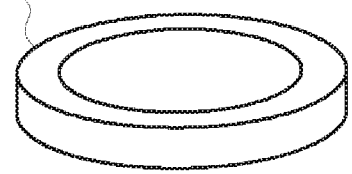
FIGS. 17A and 17B show modification of the third embodiment of present invention.
Figure 17B:
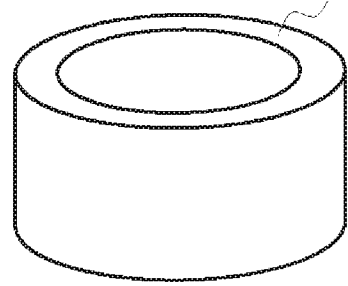

The above example used a triangle shape guiding member, and the shape can be others such as circle, donuts, rectangular, oval etc. For example, as shown in FIG. 17A, when donuts shape guiding member 41 is used, donuts shaped three-dimensional cellular structure is obtained.

Figure 18:
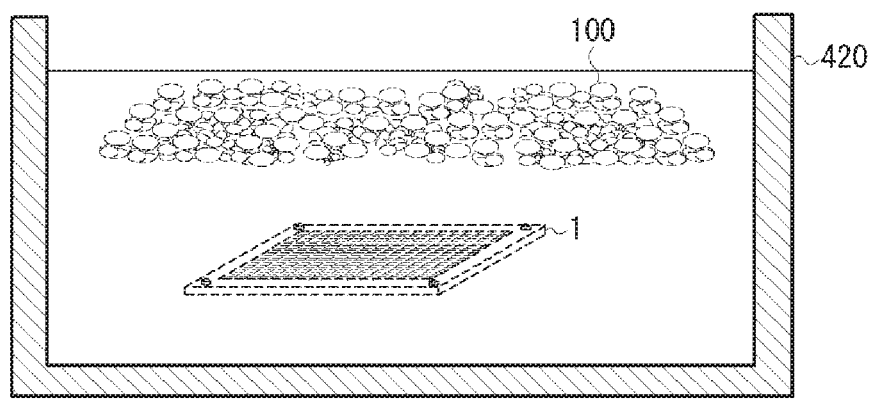
FIG. 18 explains a fabrication method of three-dimensional cellular structure by the fourth embodiment of present invention.

Next, fourth embodiment of present invention is explained. Embodiment 1-3 used dispenser to fill in cell aggregate onto supports, while fourth embodiment use process to filter out cell aggregate in solution by support. One example is shown in FIG. 18. As shown in this figure, solution containing cell aggregate 100 is held in a container, support 1 filters out cell aggregate from solution. From this procedure, cell aggregate larger than the size of net shaped space of string member 20 is filtered out onto string member.

In the case of supports with uniform size of net shaped space on string member 20 are used, the effect is identical to the process of dispensing cell aggregate of the size larger than the net shaped space onto support. Also, it is possible to filter out whole cell aggregate without exception by using supports with different size of net shaped space formed by string member.

Figure 19A:
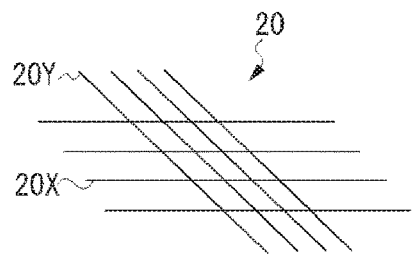
FIGS. 19A-19H explain a fabrication method of three-dimensional cellular structure by the fifth embodiment of present invention.
Figure 19B:
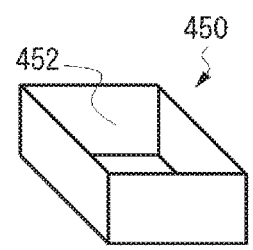
Figure 19C:
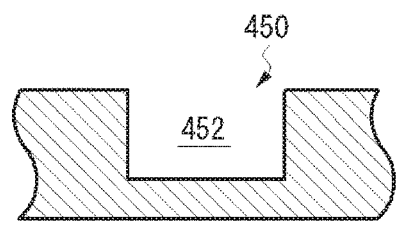

Next, a fifth embodiment is explained. The fifth embodiment is to make three-dimensional cellular aggregate by net molding process. FIGS. 19A-19H show an example of embodiment. Prepare string member which is capable to form net shaped space as shown on FIG. 19A, and prepare mold 450 in shape as shown in FIGS. 19B and 19C. Mold 450 can be any shape, and this example has rectangular shape mold 452. Mold 450 can be made by various process, and this can be made by plastic injection process. It is also possible to form mold 450 by laser processing, punching process.

Figure 19D:
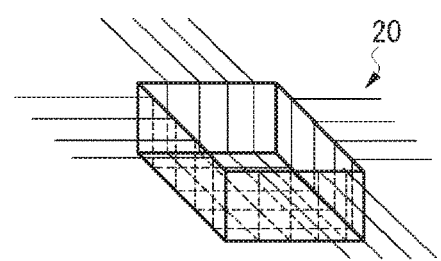
Figure 19E:
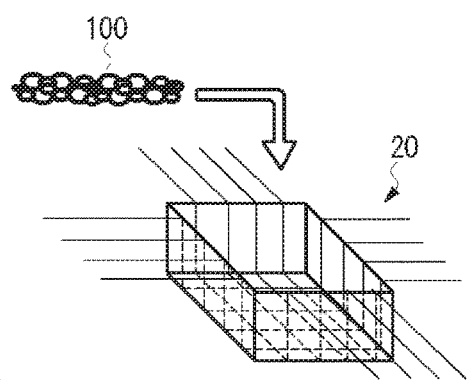
Figure 19F:
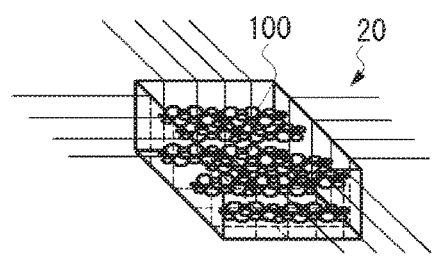
Figure 19G:
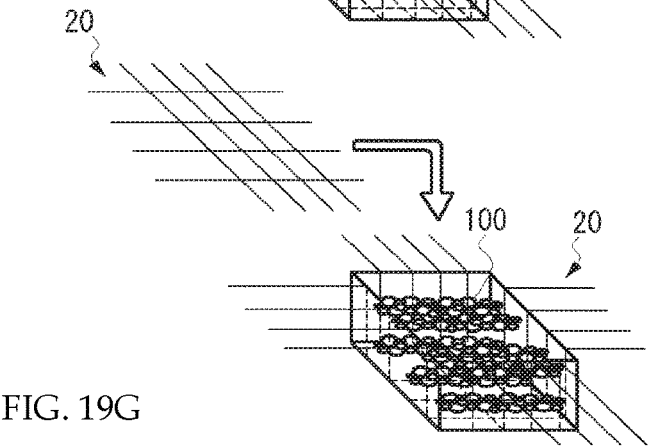
Figure 19H:
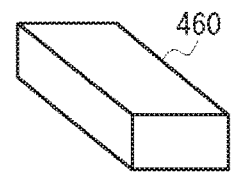

Next, as shown on FIG. 19D string member 20 is formed along the boundary of inner space 450. Next, as shown in FIGS. 19E and 19F, cell aggregate 100 is dispensed into inner space 452 of mold 450 by dispenser. Then, as shown on FIG. 19G, lid formed by string member 20, and placed onto mold 450. This lid prevents cell aggregate from spilling out from mold when shaken inside of solution with medium.

Next after cell aggregate fused together, string member 20 is lifted up from mold 450 and cell aggregate 100 is removed from mold 450. Three-dimensional cellular aggregate 460 which reflect the shape of mold 450 is obtained by removing string member 20. Preferably, string member 20 is made with non-adherent material, or its surface is coated by non-adherent material, so that removal of string member 20 from cell aggregate 100 is easier.

Figure 19I:
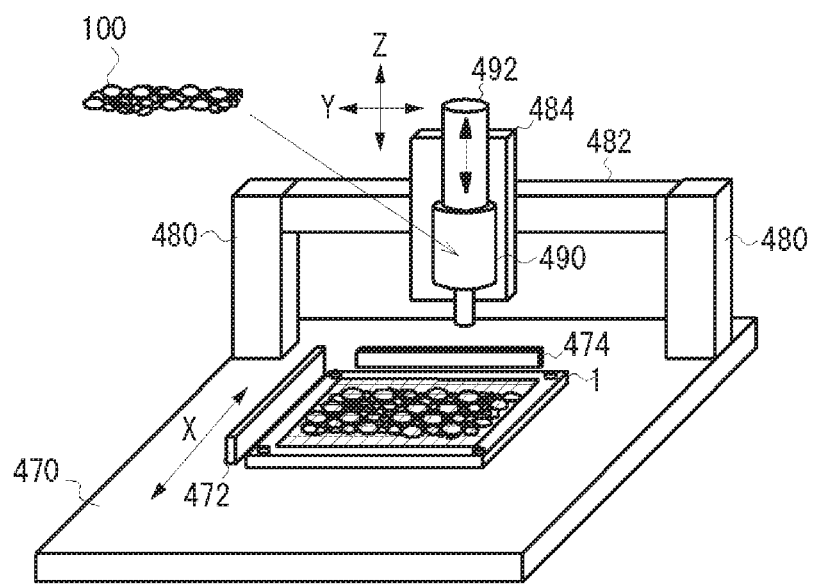
FIG. 19I explains a fabrication method of three-dimensional cellular structure by the sixth embodiment of present invention.

Next, sixth embodiment of present invention is explained. The sixth embodiment is to apply the use of support of present invention to three-dimensional dispenser. As shown on FIG. 19I, automated-dispenser comprise stage 470, reference guide 472 (x direction) and guide 474 (y direction), a pair of moving tower 480 which moves in x direction, bridging member 482 which connect between tower 480 in y direction, sliding member 484 which is movable to Y and Z direction, dispenser 490 and plunger 492 attached on sliding member 484.

Dispenser 490 will be filled with cell aggregate 100, as plunger 492 is actuated in Z direction so that cell aggregate 100 is extruded from tip of dispenser 490. Automated dispenser is pre-programmed of the shape of support 1 and the initial filling point of cell aggregate, and automated dispenser scan in X, Y, Z direction according to the three-dimensional data of three-dimensional cellular structure to be made.

After support 1 is positioned according to reference guide 472 and 474, dispenser 490 scan in direction of X and Y, simultaneously plunger 492 is actuated, cell aggregate is extruded onto support from tip of dispenser 490. When one support dispensing is completed, another support is layered and again cell aggregate is dispensed according to three-dimensional data. This embodiment enables fast dispensing of cell aggregate onto supports.

Next, several ways to fabricate support are explained. Support 1 comprises, for example, rectangular frame 10. Support 1 can be any shape and size, and space surrounded by frame 10 is further divided into smaller spaces by string member 20. String Member 20 consists of thread or needle shaped member and end of string member 20 is adhered or fixed in other way to frame.

Figure 20A:
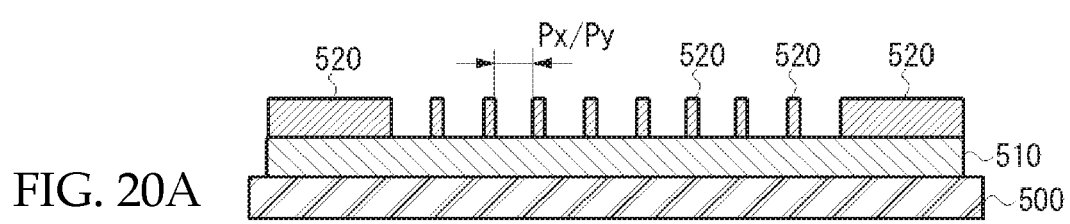
FIGS. 20A-20D provide a sectional view of support when manufactured by semiconductor manufacturing process.

Another way to fabricate support is to use semiconductor lithography process to form multiple spaces onto thin plastic or metal material. FIGS. 20A-20D show schematic cross-sectional view of the process. As shown in FIG. 20A, place thin material 510 which will become support onto resin film 500 such as UV cured type, and patterned musk 520 is formed by photo-lithography process, Musk 520 is designed so that gap distance Px, Py form matrix shape.

Figure 20B:
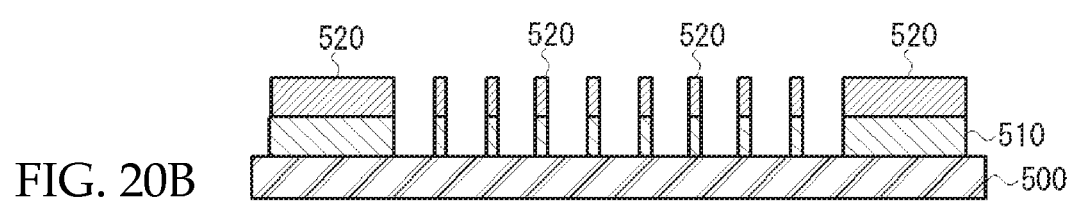
Figure 20C:
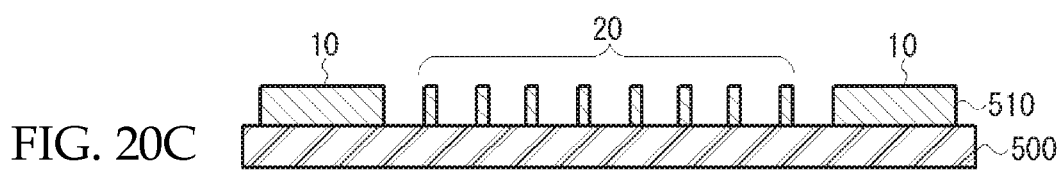
Figure 20D:
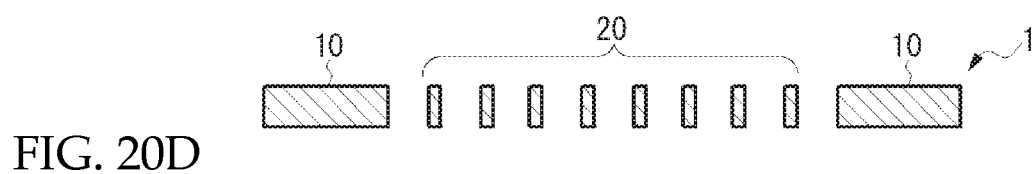

Next FIG. 20B shows that exposed areas of thin material 510 are removed by an etching process. Anisotropic etching process is preferred for accuracy. Etching process can be either wet or dry process. Next, as shown in FIG. 20C, musk 520 is removed and then as shown in FIG. 20D resin film 500 is removed by exposing to UV light.

By these processes, integrated support 1 comprising frame 10 and string member 20 as one is fabricated. Above mentioned example used photo lithography process, but musk 520 fabrication method can be other method such as laser processing.

Furthermore as other way of fabrication, cavity with gap distance Px, Py can be formed by laser processing onto thin material to form support. Also, punching process can be used to form cavity onto thin material by applying embossing member with Px, Py shaped pattern. Also, 3D printer can be used to from integrated support with frame and string member as one by resin materials.

Figure 20E:
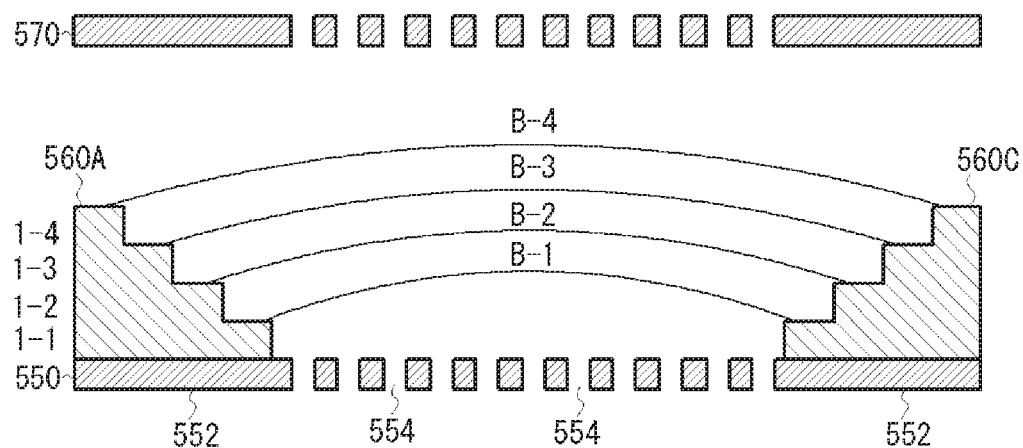
FIG. 20E shows sectional view of support when formed by bonding wire.

Other way to fabricate support, string member 20 of support can be formed by bonding wire. FIG. 20E is schematic cross-sectional view when string member is formed by bonding wires. As preferred example, base 550 is prepared first. Base 550 is made with metal material such as stainless steel. Base 520 comprise outer frame 552 and center net area which comprise multiple opening 524. As an example, opening 554 can be made by etching process on base 550. On outer frame 552, frame 560A and 560C with level step in its inside are formed. Frame 560A and 560C are equivalent to frame 10A, 10C of FIG. 1, respectively. On this example. Frame 560A and 560C possess 4 level steps equivalent to 4 layers of supports. On layer 1-1, bonding wire B-1 runs in X and Y directions, and on layer 1-2 bonding wire B-2 runs in X and Y directions, on layer 1-3 bonding wire B-3 runs in X and Y directions, on layer 1-4, bonding wire B-4 runs in X and Y directions. This structure is practically same structure as 5 supports are layered.

It is noted that the gap distance of bonding wire B-1~B-4 in X and Y direction does not have to be uniform. Similarly gap distance of opening 554 in X and Y direction does not have to be uniform. The gap distance can be various as explained in FIGS. 11A and 11B. Furthermore if necessary, top lid 570 can be used. This top lid can be same as base 550.

Figure 21:
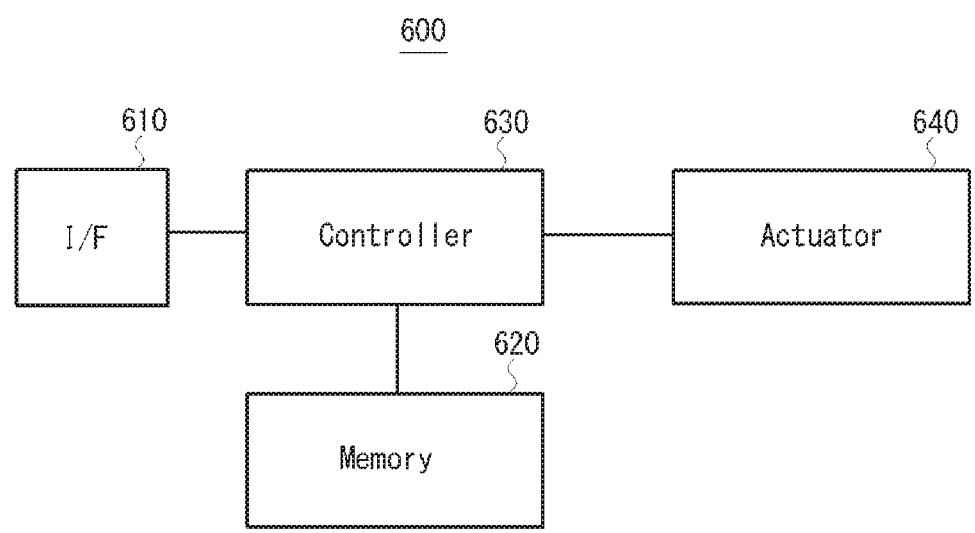
FIG. 21 shows one example of manufacturing equipment for three-dimensional cellular structure concerning embodiment of present invention.

FIG. 21 is a block chart of electrical structure of equipment used for three-dimensional cellular structure fabrication. Equipment 600 comprise interface 610 which enable input from operator and connection between equipment and peripheral equipment, memory 620 which stores data and program, controller 630, and actuator 640 which drives dispenser 200. Memory 620 comprise program for fabrication process to fabricate three-dimensional cellular structure, controller 630 conduct the program to fabricate three-dimensional cellular structure. As a preferable example, memory 620 stores 3D data of three-dimensional cellular structure, controller 630 controls scanning track of dispenser 200. This means that the dispenser provides the shape of cell aggregates on the support based on 3D data. In this case, the shape of each layer of support is determined by 3D data. For example, when 3D data is corn shape, dispenser 200 deliver cell aggregate in different shapes, which is smaller and smaller, on each layer. Also, actuator 640 moves stage to X and Y direction to dispense cell aggregate onto supports.

Figure 22A:
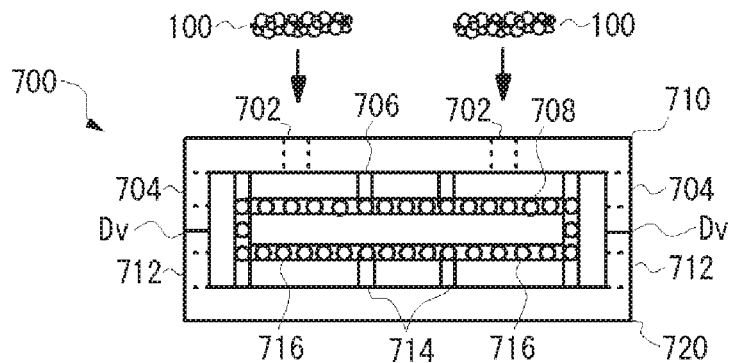
FIGS. 22A-22C show manufacturing process of support by 3D Printer concerning the sixth embodiment of present invention.
Figure 22B:
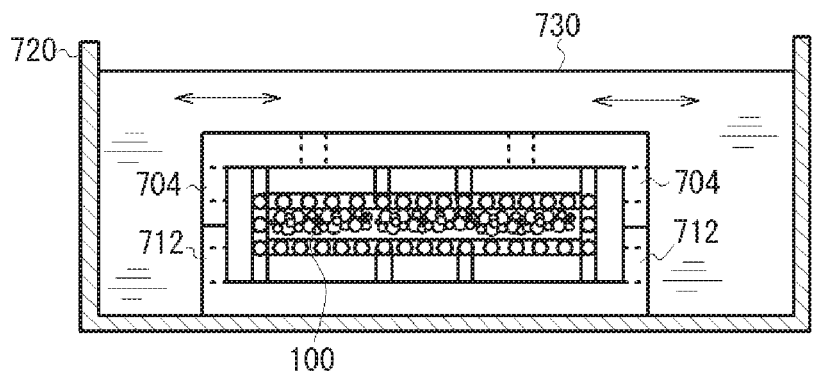
Figure 22C:
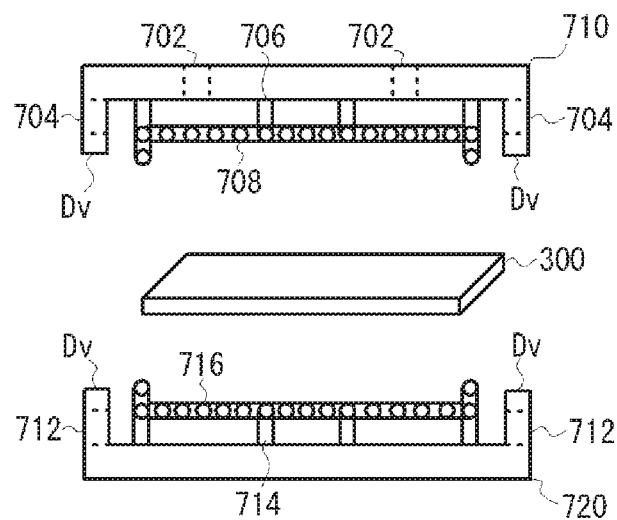

Next, the seventh embodiment is described. FIGS. 22A-22C show how 3D support is made by 3D Printer. In this embodiment, this 3D support is called as mold 700. Mold 700 is made with non-toxic material to human being. Preferably, mold 700 is made with material such as polycarbonate which has high melting temperature for high temperature sterilization. Also preferably, mold 700 is coated with non-adherent material to prevent cell adhesion to mold.

Mold 700 comprise, as shown in FIG. 22A, upper part 710 and lower part 720. Upper part 710 and lower part 720 possess net shaped area where cell aggregates are held and they are made by 3D printer. When cell aggregate is filled in mold and cell aggregate is fused, in order to remove three-dimensional cellular structure from mold 700, mold 700 is separated to upper part 710 and lower part 720 at cutting position Dv.

Upper part 710 comprises top and side members. Multiple filling holes 702 are connected to the inner space on the top member. Also, a side of upper part 710 has multiple circulation holes 704 for medium flow. Upper part 710 comprises column support 706 which extend from top, and multiple support columns 706 are connected to upper net shaped members 708 which form three-dimensional space. Lower part 720 comprise column support 714 which extend from bottom, and multiple support column 714 are connected to lower net shaped member 716 which form three-dimensional space.

Cell aggregate 100 is filled in through filling hole 702. One preferable example, the gap distance of upper net shaped member 708 is larger than the size of cell aggregate but the gap distance of lower net shaped member 716 is smaller than the size of cell aggregate so that cell aggregate pass through upper net shaped member 708 and trapped by lower net shaped member 716. It needed to be noted that this is one example and gap distance of upper net shaped member 708 and lower net shaped member can be the same.

Next, as shown in FIG. 22B, mold 700 with cell aggregates filled is soaked in container 720 filled with medium 730. By applying movement by shaker, medium 730 shall circulate through filling hole 702 and circulating holes 704 and 714, which enable effective culture of cells. When maturation is completed, as shown in FIG. 22C, mold 700 is separated to upper part 710 and lower part 720, and three-dimensional cellular structure is obtained.

String member 20 used by embodiment 1-6 are made of either adherent or non-adherent materials. Preferably, string member 20 is made with non-adherent material for easy removal, coated with non-adherent material otherwise.

Cell aggregate used by embodiment 1-3 are consists of either single cell type or multiple cell types. When multiple cell types are used, obtained three-dimensional cellular structure comprise multiple cell type.

Three-dimensional cellular structure made by embodiment 1-5 are used for medical and research purpose, as well as potential application of joint regeneration, toxicity screening, cancer research, neural regeneration, cardiovascular regeneration, as such.

Above, many embodiments are described, but should be noted that present invention is not limited to these embodiments and shall be modified within the gist of present invention as claimed in this document.

What is claimed is:

1. A method for fabricating a three-dimensional cellular structure, the method comprising:
   (a) seeding cell aggregates (spheroids) onto two or more supports, thereby obtaining a plurality of supports;
   wherein each support of the two or more supports comprises:
   a first frame placed in an x-direction, a first frame placed in a y-direction, a second frame placed in the x-direction, and a second frame placed in the y-direction, a plurality of string members placed in the x-direction, wherein each string member within the plurality of string members placed in the x-direction is connected to the first frame and the second frame placed in the y-direction, and wherein a gap distance (Px) between each string member within the plurality of string members placed in the x-direction is between about 0.01 mm and about 3 mm;

a plurality of string members placed in the y-direction, wherein each string member within the plurality of string members placed in the y-direction is connected to the first frame and the second frame placed in the x-direction, and wherein a gap distance (Py) between each string member within the plurality of string members placed in the y-direction is between about 0.01 mm and about 3 mm;

wherein the plurality of string members placed in the x-direction and the plurality of string members placed in the y-direction are perpendicular to each other in a same plane and form a plurality of rectangular net shaped or matrix shaped spaces in the same plane inside each support of the one or more support;

wherein the plurality of net shaped or matrix shaped spaces defines a plurality of physical boundaries capable of holding cell aggregates; and wherein the plurality of string members placed in the x-direction and the plurality of string members placed in the y-direction are separable from the frames;

(b) layering the plurality of supports obtained in step (a);
wherein the cell aggregates have access to nutrients and oxygen through the plurality of net shaped or matrix shaped spaces to allow for cell adhesion and fusion of the cell aggregates to each other;

(c) culturing the cell aggregates such that they fuse together forming a three-dimensional cellular structure; and (d) removing the plurality of string members placed in the x-direction and the plurality of string members placed in the y-direction inside the frames of each support within the plurality of supports from the three-dimensional cellular structure; thereby fabricating the three-dimensional cellular structure.

2. The method of claim 1, wherein the plurality of string members placed in the x-direction and the plurality of string members placed in the y-direction are made of a material that is non-adhesive with respect to the cell aggregates.

3. The method of claim 1, wherein the plurality of string members placed in the x-direction and the plurality of string members placed in the y-direction are coated with a material that is nonadhesive with respect to the cell aggregates.

4. The method of claim 1, wherein the seeding comprises loading the cell aggregates into a dispenser and triggering the dispenser to dispense the cell aggregates onto the plurality of net shaped or matrix shaped spaces.

5. The method of claim 1, wherein the seeding comprises placing a guide member onto the two or more supports of the plurality of supports, the guide member defining the shape of the three-dimensional cellular structure, wherein the cell aggregates are seeded within the guide member.

6. The method of claim 1, wherein the seeding comprises using the two or more supports of the plurality of supports to scoop up a liquid containing the cell aggregates from a container.

7. The method of claim 1, further comprising immersing the two or more supports of the plurality of supports with the seeded cell aggregates into a container holding a liquid containing nutrients and applying vibrations or swings to the two or more supports of the plurality of supports or the container.

8. The method of claim 1, wherein the removing comprises drawing the plurality of string members placed in the x-direction from the cell aggregates in the x-direction and drawing the plurality of string members placed in the y-direction from the cell aggregates in the y-direction.

9. The method of claim 1, wherein the gap distance Px is uniform.

10. The method of claim 1, wherein the gap distance Py is uniform.

11. The method of claim 1, wherein the gap distance Px is equal to the gap distance Py.

12. The method of claim 1, wherein the gap distance Px is greater than the gap distance Py.

13. The method of claim 1, wherein the gap distance Py is greater than the gap distance Px.

14. The method of claim 1, wherein a ratio between the gap distance Px and the gap distance Py is between 0.1 and 1.0.

15. The method of claim 1, wherein a ratio between the gap distance Py and the gap distance Px is between 0.1 and 1.0.

16. A method for fabricating a three-dimensional cellular structure, the method comprising:

(a) layering two or more supports, thus obtaining a plurality of layered supports;
wherein each support of the two or more supports comprises:
a first frame placed in an x-direction, a first frame placed in a y-direction, a second frame placed in the x-direction, and a second frame placed in the y-direction, a plurality of string members placed in the x-direction, wherein each string member within the plurality of string members placed in the x-direction is connected to the first frame and the second frame placed in the y-direction, and wherein a gap distance (Px) between each string member within the plurality of string members placed in the x-direction is between about 0.01 mm and about 3 mm;

a plurality of string members placed in the y-direction, wherein each string member within the plurality of string members placed in the y-direction is connected to the first frame and the second frame placed in the x-direction, and wherein a gap distance (Py) between each string member within the plurality of string members placed in the y-direction is between about 0.01 mm and about 3 mm;

wherein the plurality of string members placed in the x-direction and the plurality of string members placed in the y-direction are perpendicular to each other in a same plane and form a plurality of rectangular net shaped or matrix shaped spaces in the same plane inside each support of the one or more support;

wherein the plurality of net shaped or matrix shaped spaces defines a plurality of physical boundaries capable of holding cell aggregates; and wherein the plurality of string members placed in the x-direction and the plurality of string members placed in the y-direction are separable from the frames;

(b) seeding cell aggregates onto the plurality of layered supports obtained in step (a);
wherein the cell aggregates have access to nutrients and oxygen through the plurality of net shaped or matrix shaped spaces to allow for cell adhesion and fusion of the cell aggregates to each other;

(c) culturing the cell aggregates such that they fuse together forming a three-dimensional cellular structure; and (d) removing the plurality of string members placed in the x-direction and the plurality of string members placed in the y-direction inside the frames of each support within the plurality of supports from the three-dimensional cellular structure; thereby fabricating the three-dimensional cellular structure.

17. The method of claim 16, wherein the seeding comprises loading the cell aggregates into a dispenser and triggering the dispenser to dispense the cell aggregates onto the plurality of net shaped or matrix shaped spaces.

18. The method of claim 16, wherein the seeding comprises using the plurality of supports to scoop up a liquid containing the cell aggregates from a container.

19. The method of claim 16, further comprising immersing the plurality of layered supports with the seeded cell aggregates into a container holding a liquid containing nutrients and applying vibrations or swings to the plurality of layered supports or the container.

20. The method of claim 16, wherein removing comprises drawing the plurality of string members placed in the x-direction from the cell aggregates in the x-direction and drawing the plurality of string members placed in the y-direction from the cell aggregates in the y-direction.

* * * * *